(12) United States Patent
Paulson

(10) Patent No.: US 11,083,627 B2
(45) Date of Patent: Aug. 10, 2021

(54) EYE HYDRATION DEVICE ADAPTED FOR EMPLOYMENT WITH CPAP

(71) Applicant: Suzanne Paulson, Temecula, CA (US)

(72) Inventor: Suzanne Paulson, Temecula, CA (US)

(*) Notice: Subject to any disclaimer, the term of this patent is extended or adjusted under 35 U.S.C. 154(b) by 0 days.

(21) Appl. No.: 14/425,262

(22) PCT Filed: Feb. 27, 2015

(86) PCT No.: PCT/US2015/018174
§ 371 (c)(1),
(2) Date: Mar. 2, 2015

(87) PCT Pub. No.: WO2015/131145
PCT Pub. Date: Sep. 3, 2015

(65) Prior Publication Data
US 2016/0354250 A1 Dec. 8, 2016

Related U.S. Application Data

(60) Provisional application No. 61/945,688, filed on Feb. 27, 2014.

(51) Int. Cl.
A61F 9/04 (2006.01)
A61M 16/06 (2006.01)
A61F 9/00 (2006.01)

(52) U.S. Cl.
CPC ........... A61F 9/04 (2013.01); A61M 16/0683 (2013.01); A61F 9/00 (2013.01); A61M 16/06 (2013.01); A61M 2210/0612 (2013.01)

(58) Field of Classification Search
CPC ...... A61F 9/00; A61F 9/02; A61F 9/04; A61F 13/02; A61F 13/12; A61F 13/124;
(Continued)

(56) References Cited

U.S. PATENT DOCUMENTS 4,688,567 A * 8/1987 Kikuchi ............... A62B 18/025
128/206.15
5,307,095 A 4/1994 Ogura
(Continued)

OTHER PUBLICATIONS

"Planar". Dictionary.com, http://www.dictionary.com/browse/planar, p. 1 definition 2.*
(Continued)

Primary Examiner — Rachael E Bredefeld
Assistant Examiner — Rachel A Berezik
(74) Attorney, Agent, or Firm — Donn K. Harms

(57) ABSTRACT

An device for maintaining a moisture cavity surrounding the eye of a user is provided which employs a flexible body configured for positioning on the face of the user with a cavity defined by a curved sidewall positioned in front of each eye of the user. The cavity prevents communication of the exterior atmosphere with the air within the cavity and thereby maintains an environment in each cavity suitable to maintain natural eye moisture. The body is configurable to engage to the face of the user concurrent with the engagement of a CPAP device and may be adapted for engagement as part of the CPAP device. Curved sidewalls forming each cavity are optically correct and transparent to maintain the vision of the user during use.

20 Claims, 5 Drawing Sheets

(58) Field of Classification Search
CPC .................. A61F 5/56; A61F 2007/02; A61F 2007/0004; A61F 9/026; A61F 9/028; A61F 9/029; A61M 16/06; A61M 16/0683; A61M 2210/0612; A61M 16/0627; A61M 16/0605; A61M 16/0666; A61M 16/0688; G02C 3/00; G02C 3/003; G02C 3/008; G02C 3/006; G02C 3/02; A62B 18/00; A62B 18/025; A62B 18/082; A61B 18/088; A63B 33/002; B63C 11/12
See application file for complete search history.

(56) References Cited

U.S. PATENT DOCUMENTS

| | | | | |
|---|---|---|---|---|
| 5,425,380 | A * | 6/1995 | Hudson | A61F 9/026 128/858 |
| 6,776,485 | B2 * | 8/2004 | Cole | G02C 11/00 248/902 |
| 7,231,922 | B2 * | 6/2007 | Davison | A61F 9/029 128/858 |
| 2006/0231097 | A1 | 10/2006 | Dougherty et al. | |
| 2007/0252946 | A1 * | 11/2007 | Welchel | A41D 13/1184 351/62 |
| 2008/0257362 | A1 * | 10/2008 | Davison | A61F 9/02 128/858 |
| 2010/0199411 | A1 * | 8/2010 | Kaiser | A61F 9/04 2/440 |
| 2013/0019374 | A1 * | 1/2013 | Schwartz | A61F 5/00 2/69 |
| 2013/0255697 | A1 * | 10/2013 | Thompson | A61F 9/04 128/858 |
| 2014/0373846 | A1 * | 12/2014 | Kao | A62B 7/10 128/204.23 |

OTHER PUBLICATIONS

"Flange". Dictionary.comm http://www.dictionary.com/browse/flange, p. 1 definition 1.*

* cited by examiner

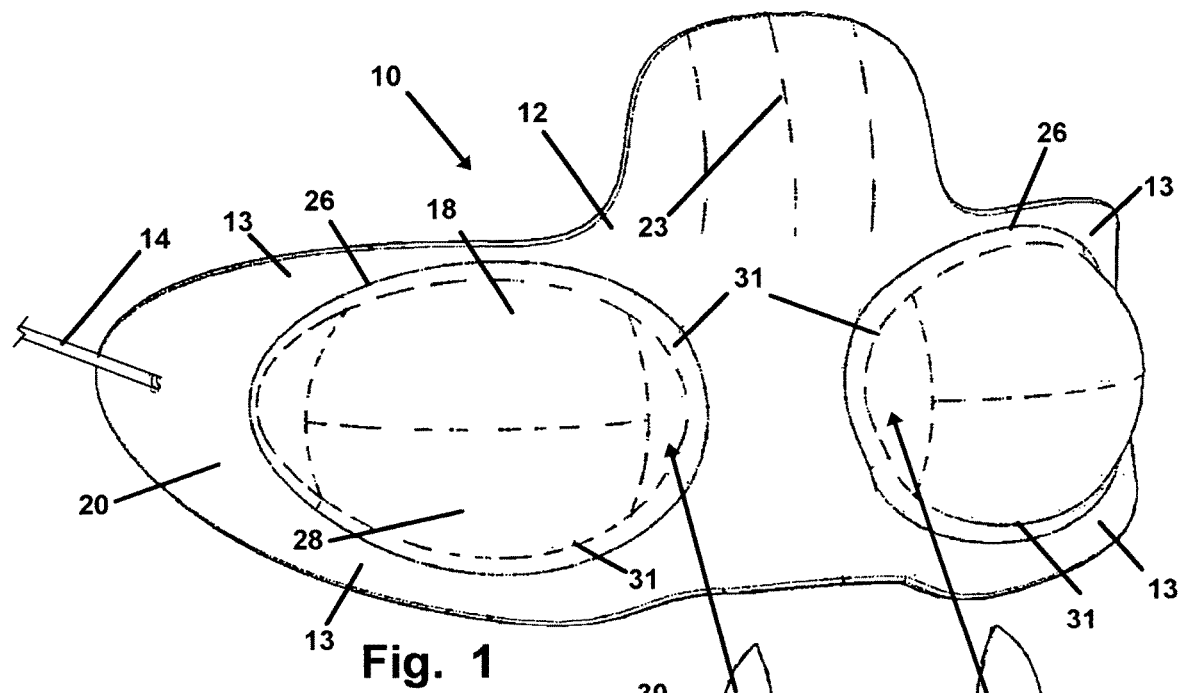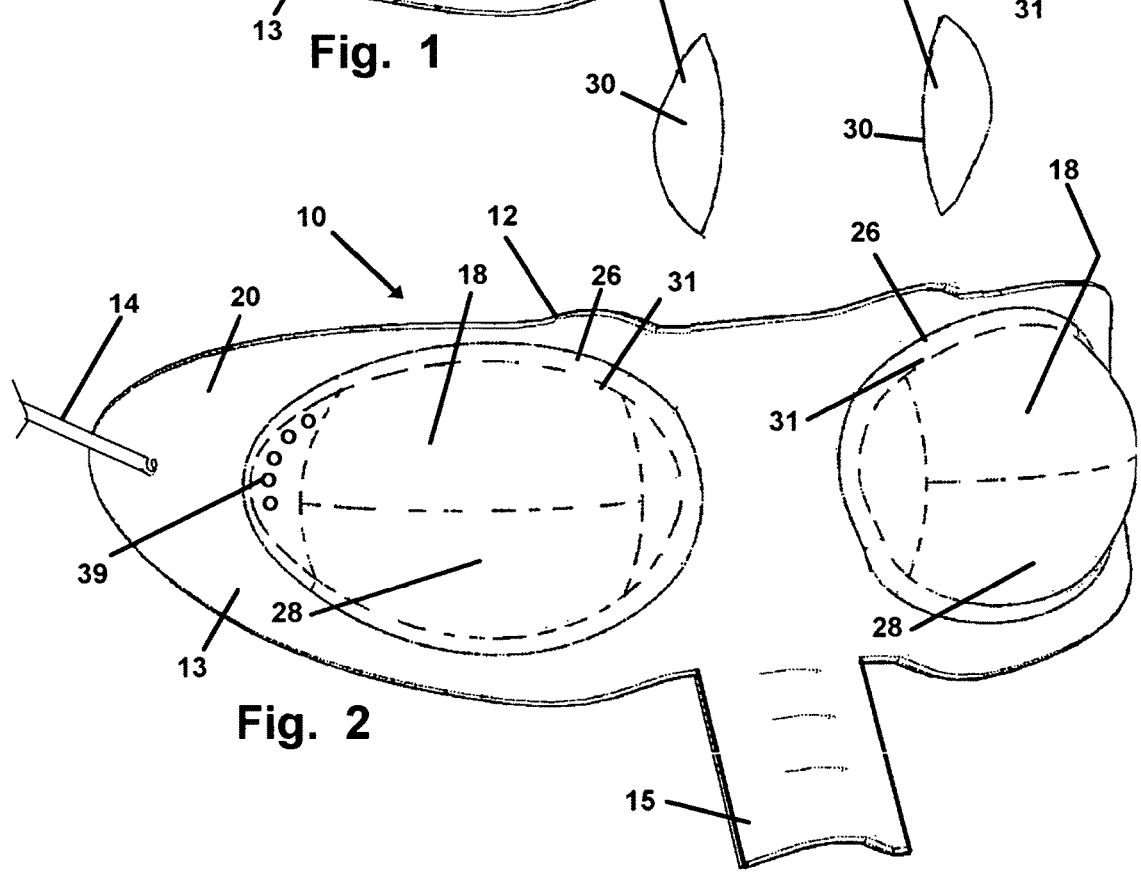

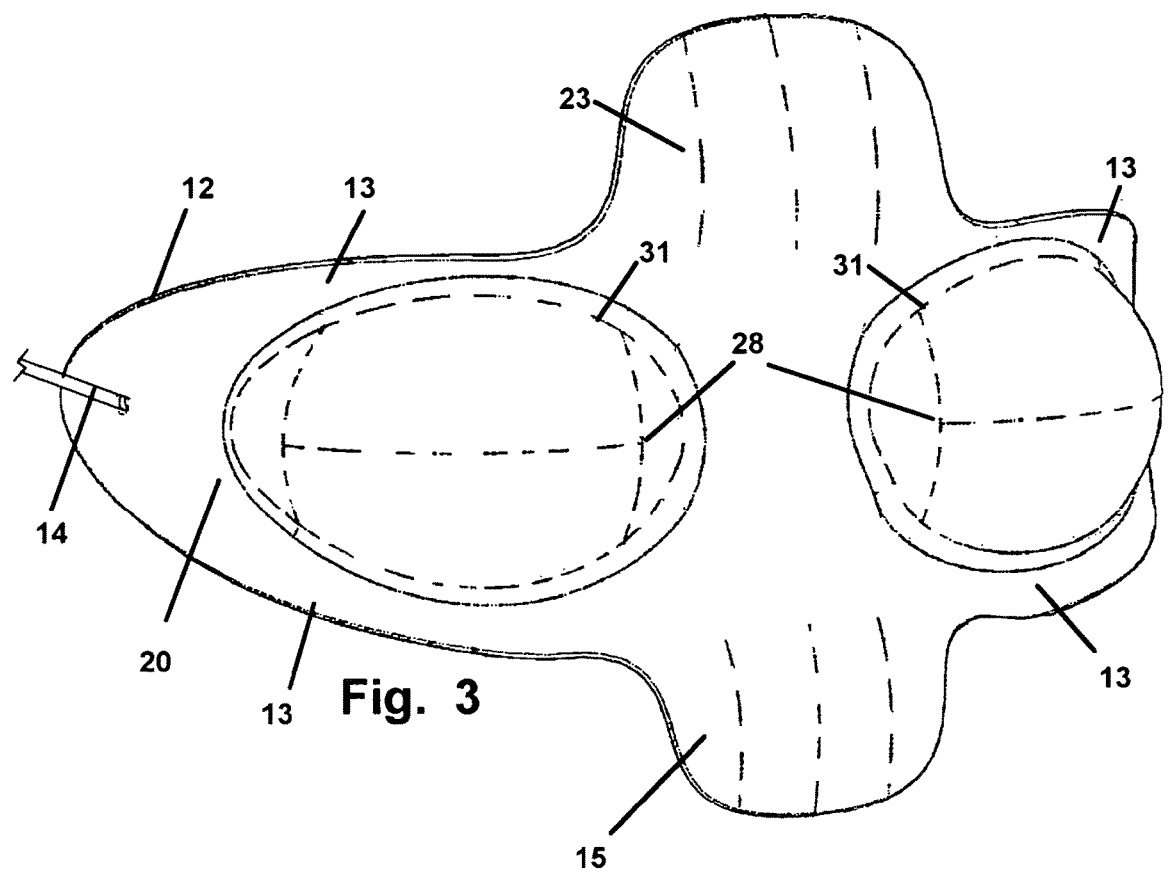
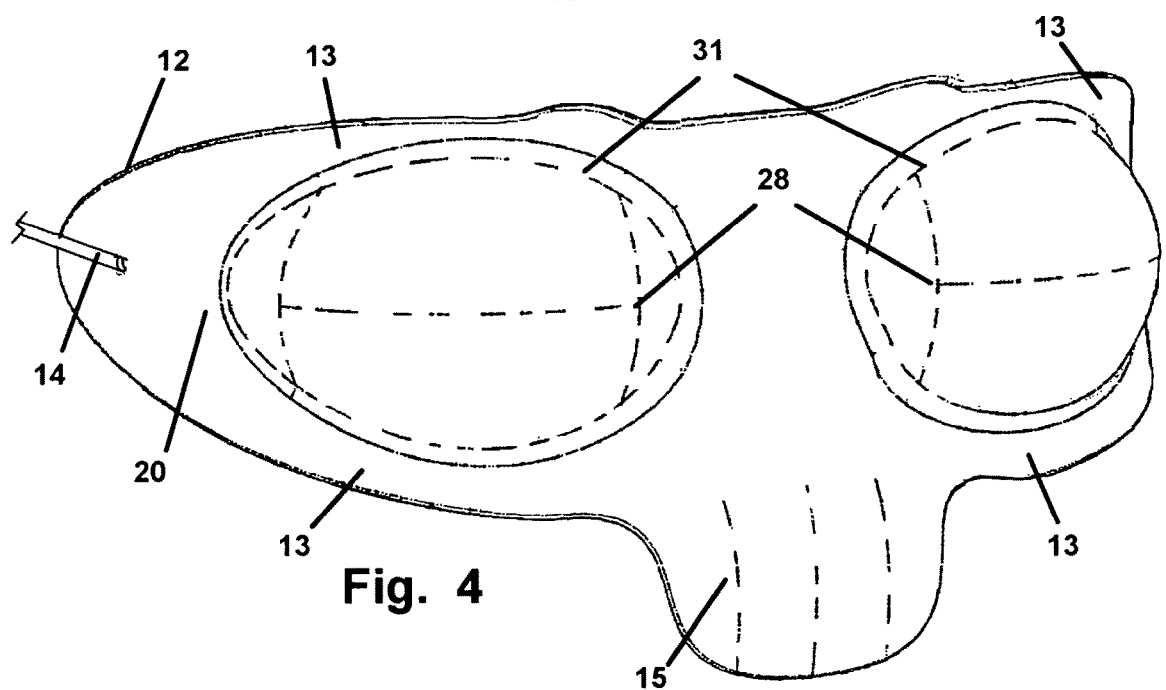

EYE HYDRATION DEVICE ADAPTED FOR EMPLOYMENT WITH CPAP

This application claims priority to U.S. Provisional Application No. 61/945,688 filed on Feb. 27, 2014, and is incorporated herein by this reference. The disclosed device and method relates to a system for sheltering the surface of the eyes during regular sleep, or especially when sleeping wearing a CPAP device. The soft flexible mask disclosed is configured to form moisture retaining cavities in a sealed engagement with face area surrounding the eyes of the wearer and thereby maintain the tear film on the eyes and a humid surrounding air pocket in the cavity in communication with each eye. The device is effective for normal sleeping individuals whether in bed or on a plane or the like, and is especially beneficial when employed in combination with the wearing of a CPAP device by the user.

FIELD OF THE INVENTION

Background of the Invention

Sleep apnea is a type of sleep disorder suffered by millions of people worldwide. Generally, sleep apnea is characterized by pauses in breathing of a sleeping person or instances of shallow or infrequent breathing during sleep. Every cessation or pause in breathing is called an apnea and such can occur in durations which vary from eight to ten seconds to several minutes. These breathing cessations may occur five to thirty times or more per hour which can severely lower the oxygen levels in the blood of sufferers leading to other medical problems. Similarly, each abnormally shallow breathing event is called a hypopnea.

Patients suffering from sleep apnea prior to any treatment tend to have severe problems resulting from sleep deprivation. This is because when a patient suffering from sleep apnea ceases breathing and frequently the only urge to start breathing again occurs as the patient awakes sufficiently from oxygen deprivation to start breathing again. This awakening occurs because the oxygen level in the patient's blood is so low that it causes a person to become startled and to awake gasping for air. This pattern repeats itself all night long whereby patients suffering from sleep apnea awaken exhausted, and have severe concentration problems and are a significant risk to others when driving due to the tendency to nod off.

There are a number of forms of sleep apnea, but regardless of type, an individual with sleep apnea is rarely aware of having difficulty breathing, even upon awakening. Sleep apnea is usually recognized as a problem by others witnessing the individual during episodes or is suspected because of its effects on the body. Without treatment, symptoms may be present for years (or even decades) when the problem remains unidentified.

Other than surgery which most patients decline, the only treatment available is using a continuous positive airway pressure device which is conventionally known by the acronym "CPAP" device, when sleeping. CPAP treatment communicates a continuous positive air pressure stream directly to the mouth and nose of the patient. The incoming airstream communicated through a hose and mask in a sealed engagement with the nose and mouth of the patient, is under positive pressure above atmospheric pressure and thus maintains a continuous level of positive airway pressure in a breathing patient. This increased pressure is provided by a ventilator device engaged to a hose which is in sealed communication with a mask positioned in a seal over the mouth and nose of the face of the patient.

While CPAP devices have helped many apnea sufferers with the problems associated with constant breathing cessation, is has become known such device frequently cause many users discomfort. The discomfort increases especially after hours of engagement of the CPAP device.

Because of the constant positive air pressure being communicated to the mask covering the patient's mouth and/or nose, a continuous problem frequently occurs with leakage of an air stream from between the mask edge, and the face of the patient. Because of the contour of the nose of most users where the nose meets their face, and the marginal seal that is created in this area on both sides of the nose by a CPAP mask, a constant problem with air leakage occurs adjacent the eyes of users of CPAP machines. This leaking moving airstream when it moves against or over the eyes of the user, frequently causes dry eyes on patients using CPAP machines. Dry eyes, can cause other problems for the patient medically such as the inability to lubricate the eye during movement which occurs during sleep. This eye movement in dry unlubricated contact against the eyelid, can be painful. Further the lack of a tear film on the eyes impairs the natural cleaning of the eye surface of dust and leading to a gathering of such on the dry surface of the eye.

It is little known, but most people, never totally shut their eyes during sleep. The small gap between the closed eyelids of the eyes which is present during sleep combined with the moving air stream from the mask, traveling across the user's eyes, continuously evaporates the moisture on the eye surface in a manner where it cannot be replenished. Further, moving airstreams serve to deposit dust and particulate on the eye surface.

To date, one manner to prevent this dry eye problem is for patients to cease using the CPAP machine which is unacceptable for any long duration. Alternatively, they can tighten the mask so taught against the face, that the air leakage ceases. However a very tight CPAP mask, worn for six to eight hours of slumber, can be terribly uncomfortable and a poor solution.

A further problem exists where sleeping persons sleep under an overhead fan, or with a fan blowing upon them, or in venues with extremely dry air such as an airplane during flight. Because sleeping individuals do not completely close their eyes during sleep, a small opening between the lid and lower eye generally persists during sleep. Just as with leaking moving air from a CPAP device, dry and/or moving air contacting the face of a sleeping individual, will cause a similar eye drying problems as that of the CPAP machine.

As such, there is an unmet need for a device that both shields the eyes of CPAP users from ongoing airstreams as individuals just sleeping in venues with fans and dry air such as from air conditioners. Such a device should additionally aid in hydrating the eyes and surrounding face tissue of a patient, while they are sleeping with a CPAP device engaged or adjacent a moving fan or forced air device.

The device and method described herein, developed after experimentation in numerous modes, solves the shortcomings of CPAP use relating to dry eyes and accordingly comprises and provides the elements and features of such a device, in the construction, use, combination of elements, and arrangement of parts, which will be exemplified by the constructions hereinafter set forth, and the scope of the invention will be indicated in the claims.

SUMMARY OF THE INVENTION

The disclosed device and method, provides a face mask style component configured to shield the eyes from moving and dry air which as noted is a significant problem for many sleeping individual. Rather than just form a barrier in front of each eye which was initially found to improve eye dryness, after a number of less than successful attempts it was found that including individual eye shields which define treatment cavities in substantially sealed engagements with each eye, provided a solution to the dry eye symptoms of sleeping individuals. This sealed cavity is enabled through a seal formed around each eye socket with the surrounding tissue of the eyes of a user or patient. These individual chambers when sealed around each eye of the patient, provide a shield to the surface of the eye, from escaping airstreams from the CPAP mask and from cold temperatures or air which is dry in nature.

Each of the chambers engaged with an annular sealing flange surrounding each eye of the user thereby forms an individual sealed chamber defined by the interior wall of the device, the eye surface and the skin surrounding the eye surface within the seal. Each chamber maintains a hydrated atmosphere to the area of the eyes and surrounding skin of the patient within the annular seal in operative engagement on the face. So engaged, the chamber formed provides a total shield from airstreams generated by the CPAP mask and a means for maintaining the eyes in a controlled atmosphere which may be placed in a hydrated and heated, or cooled condition.

The eye chambers formed of rigid and semi rigid plastic were found to work to form such chambers, however the patients found them less than comfortable when sleeping, especially if the face were in contact with the bedding for any period of time. Additionally, many patients found the lenses or shields claustrophobic if they were tinted or otherwise rendered unclear.

A configuring of the device with shields formed of substantially transparent polymeric or plastic material whereby the user when wearing the mask, can see through the wall of the eye chamber opposite each eye has been found to be preferred in all modes of the device herein. Such materials can include polymeric materials such as silicone, thermal plastic, or other soft, flexible material which will remain comfortable to wear during a night of sleep. An annular base section or flange extends from the circumference of the base of each chamber which is preferably soft and elastic to provide both a good seal against the skin of the patient in the eye socket surrounding the eye of the patient as well as a comfortable fit, and an adjustable fit since the flange will stretch to conform to the adjacent shape of the face.

Engagement of the mask to the face of the user can be held using a strap or other flexible member which engages between two ends of the mask and around the rear of the head of the wearer. This engagement has been found to work well when the user is not wearing a CPAP mask, and to be acceptable when a CPAP is being worn.

However, it has been found that during sleep, a shifting of the CPAP device in an engagement with the face of the user can move the mask device herein. Consequently, the shielding eye mask herein if configured for operative engagement in combination with the CPAP has been found to be preferable. In this mode the eye mask herein is positioned to the as-used position on the face concurrently with the placement of the CPAP mask on the face. This has found to work well with a simple sandwiched engagement of the eye shielding mask herein between the CPAP and face, as well as using straps, hook and loop fabric, magnets, and other releasable complimentary fasteners of the eye shield mask herein and a CPAP device.

In all modes of the device herein, a respective one of the two chambers of the mask are placed in a respective sealed engagement in front of a respective one eye of the user. A strap, or connection to the CPAP device, or other means to bias a soft flange of the device against the user's face is employed to hold the device in an as-used position.

In other modes the device is employed without a strap around the head and may be attached directly to the CPAP device or mask, or to the headgear that is used to attach the CPAP device or may be formed as a unitary structure, with the CPAP mask. The perimeter of the device may be adapted for such engagement depending on the brand and configuration required for such.

The chambers formed by the sealed soft and elastic flange and the curved shield, may simply be positioned to shield the user against escaping air from the CPAP mask, or that of a fan or air conditioner or the like. In an alternative mode, the formed chambers may include a component therein to maintain a moist atmosphere within each chamber. Moisture may be maintained and/or imparted to each chamber by the positioning of a moisture-laden pad within the chamber. The pads should be preferably configured in shape and size to maintain the user's view through the wall forming the chamber by forming the pads to be positioned upon the wall, but substantially out of the optic or normal view of the user.

Still further the moisture pads may be configured to emit warmth or warm moisture using a chemical reacting insert therein or cold and cold moisture using cooling components. Such packs could for instance employ sodium acetate, glycerin, gel packs, cold water packs, etc. to provide cold, or heat, or moisture depending on the user's needs.

Thus, with the facemask herein disclosed in an as-worn position, with both eye chambers having a soft flange in sealed engagement with the skin surrounding the eye socket of each respective eye, the moisture pads may be engaged and if desirable or a warming or thermal type of moisture pack may be engaged. Whatever may be engaged is preferably attached in a position out of the user's view so that if they awaken and need to get out of bed they can see easily through the wall of the chamber.

The facemask device herein is formed of a contacting wall or flange having a first surface which contacts the user's face and which is flexible and preferably elastic. It has been found that a material with a shore of Shore 5A to Shore 90A works well to provide soft contact and sufficient flexibility and elasticity to form a comfortable seal with the face. A current preferred material for the body, flange, and curved sidewalls is Thermoplastic Elastomer. (TPE) with the body, flange and sidewalls formed as a unitary structure in a thickness between 050" to 0.080" with a particularly preferred thickness of 0.062". Such allows for an elastic pliable flange as well as the sidewalls forming the cavities to be transparent and deform when necessary and return to the curved configuration thereafter. A sealed engagement around the eye sockets is achieved with the flexible first surface of the extending flange contacting the face and held in the as-worn position by a strap, a CPAP mask, or both. Experimentation with differing modes of the device has shown that a diameter of the flange portion should be at least ¼ inch at any narrow point and at a widest diameter less than 1½ inches to allow for the best seal and comfort in the contours of the user's face.

A sidewall forming each chamber engages with the flange at a perimeter base of each curved and projecting sidewall. The sidewall as noted is preferably soft material such that it will deform when positioned between the face of the user and bedding. However it should be formed with a memory to cause the sidewall to return the projecting curve forming the cavity in front of each eye. The sidewall defining the curved projecting cavity may be formed of the same material as the flange in a unitary structure also. Such a formation has been found allow the flange to stretch and bend to the contours of the face during engagement, but allow the sidewalls forming the chambers to substantially maintain their shape and volume and is a preferred mode.

Transparent material, preferably optically correct such that the user's normal vision is substantially maintained through the sidewall forming the shield is desired to allow the user to see through the device. In some cases it has been found that opaque material may also be employed for the sidewall forming the shield as it is especially good to use for those suffering with Lagophthalmos (partial lid closure) of the eyes, and needing more darkness for improved sleep patterns, or for individuals who which to darken their environment artificially such as when employing the device on an airplane during sleep.

Thus, when the mask is in the as-worn position, with the apertures formed at an engagement point of the sidewall forming a shield and the flange, surrounding each eye, a chamber is formed in front of each eye. The interior volume or area is defined by the front of the eye and the interior of the curved sidewall projecting away from the eye from its engagement with the flange of the flexible mask.

In one mode, an extending flap from the flexible first surface is positioned to align with the bridge of the user's nose. With the mask in the as-worn position on their face the flap provides a pad for contact with the CPAP mask and makes the CPAP mask more comfortable to wear. A second flap or extension of the edge of the mask toward the hairline of the wearer can provide a means to engage the device in a sandwiched engagement between a CPAP mask and the forehead. Alternatively, secondary straps, magnets, hook and loop fabric, or other separable fasteners may be employed with one half on the mask and the mating half of the separable fastener on the CPAP device.

In one mode of the device, the curved sidewall defining the interior cavity may have apertures therein allowing communication of air into the chambers in front of each eye. These apertures would be on a side edge of the curved sidewall, opposite the bridge of the user's nose with the mask in the as-worn position so that air escaping from the CPAP mask edges, has no chance of contact with the apertures and thus cannot communicate into the chamber in front of each eye. Finally, one other mode of the device may be employed where the protective mask is formed as part of or a component of the CPAP device.

With respect to the above description, before explaining at least one preferred mode of the herein disclosed face mask device and method in detail, it is to be understood that the invention is not limited in its application to the details of construction and to the arrangement of the components in the following description or illustrated in the drawings. The facemask invention herein described is capable of other embodiments and of being practiced and carried out in various ways which will be obvious to those skilled in the art. Also, it is to be understood that the phraseology and terminology employed herein are for the purpose of description and should not be regarded as limiting.

As such, those skilled in the art will appreciate that the conception upon which this disclosure is based, may readily be utilized as a basis for the designing of other facemask structures, methods and systems for carrying out the several purposes of the presently disclosed device. It is important, therefore, that the claims be regarded as including such equivalent construction and methodology insofar as they do not depart from the spirit and scope of the present invention.

It is an object of this invention to provide a mask which positions shielded cavities over both eyes of a user protecting them from drying air streams.

It is an additional object of this invention to provide engageable moisture pads which are easily engaged in positions out of the forward eyesight of a user wearing the face mask.

It is a further object of this invention to provide such a facemask which may be engaged to a CPAP mask using separable fasteners in positions adapted for such engagement or may be worn independent of a CPAP mask, or formed as a unitary structure with a CPAP mask.

These together with other objects and advantages which become subsequently apparent reside in the details of the construction and operation as more fully hereinafter described and claimed, reference being had to the accompanying drawings forming a part thereof, wherein like numerals refer to like parts throughout.

BRIEF DESCRIPTION OF THE DRAWING FIGURES

In the drawing figures, which are not to scale and which are merely illustrative and wherein like reference characters denote similar elements throughout the several views:

FIG. 1 is a front perspective view of a mode of the facemask apparatus formed of a flexible flange portion and having two curved sidewalls in sealed engagement with eye apertures formed in the body of the facemask.

FIG. 2 is a view of another mode of the device wherein the facemask has a projecting flexible member portion extending from the flange in a position aligning with the user's nose when worn to provide both a pad and engagement with the engaged CPAP mask.

FIG. 3 is a front perspective view of another mode of the facemask apparatus similar to that of FIGS. 1 and 2 but having a secondary member portion extending away from the flange in an opposite direction.

FIG. 4 is a front perspective view of another mode of the facemask apparatus similar to that of FIGS. 1 and 2 but having a wider first projecting portion for additional padding when used with a CPAP.

DETAILED DESCRIPTION OF THE PREFERRED EMBODIMENTS OF THE INVENTION

Figure 5:
FIG. 5 depicts a user attempting sleep with a conventional CPAP device and showing the exposed eyes adjacent the CPAP device.

Referring now to the drawings of FIGS. 1-11 there are shown various aspects of the device 10 and method herein. Shown in FIG. 1 there can be seen a perspective view of the mask 12 of the device 10, as it would be held in a biased engagement of a flange 13 portion of the body 20 against a user's face, to form individual substantially sealed controlled environments in front of each respective eye.

The device 10 may be held in the biased engagement against the face by a flexible member such as a strap 14, or operatively engaged using fasteners engaged between positions on the separable fasteners a face-affixed CPAP mask 21 (FIG. 5 or 6), or both. The fasteners 17 engaged between the CPAP mask 21 and the body 20 of the mask 12 may be separable where complimentary halves are respectively engaged in mating positions upon the CPAP mask 21 and the body 20 of the mask 12. Alternatively, the fasteners 17 may be permanent such as sewing, grommets, riveting, screws, or other permanently engaged, or separable fasteners as might be employed by those skilled in the art and found in the W.W. Grainger, Inc. catalog sections of permanent or separable fasteners.

Figure 6:
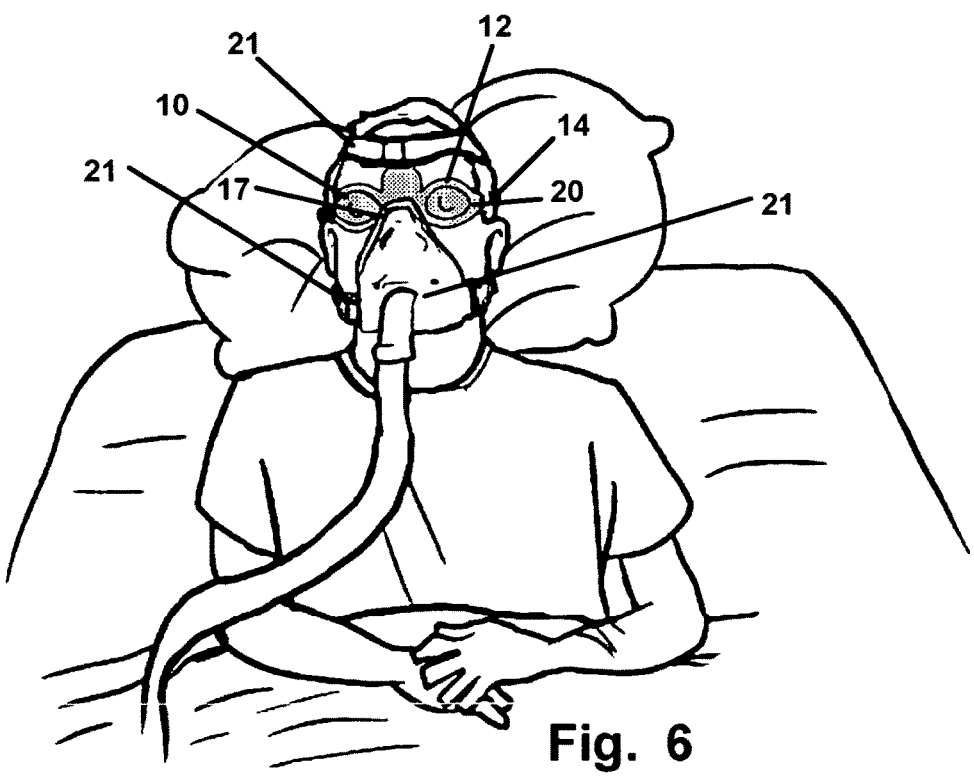
FIG. 6 depicts a user as in FIG. 5 having a CPAP device engaged while in bed and having the device herein operatively engaged to the face in an as-used position to maintain eye moisture.

Whether held by a strap 14 or fasteners 17 of a permanent or separable configuration, or combinations thereof, the device 10 is held in position with a first surface 35 in a contact forming a seal with the face of a user in the as-worn position during use such as in FIG. 6, or may simply be held by a strap 14 without the CPAP 21 device. In the as-worn position, each of two chambers 18 or moisture cavities formed by a curved sidewall 28, is aligned with a respective one of the user's eyes. This forms an individual respective sealed moisture cavity or chamber 18 aligned in front of each eye 27 (FIG. 5), and held in a sealed engagement by the seal formed with the contact of the first surface 35 of the body 20 surrounding the apertures 31 and the flexible and preferably elastic flange 13 of the body 20 of the mask 12 which extends inward from the entire perimeter edge 33 of the body 20. This flange 13 has a width at least as wide as a diameter D of the flange extending from that perimeter edge 33, to the sealed engagement of the base edge or circumference 26 of each sidewall 28 with the eye-surrounding apertures 31.

Each aperture 31 is the sealed engagement the base edge or circumference 26 of a curved sidewall 28 forms a respective substantially sealed chamber 18 or moisture chamber in front of each eye of the user. This sealed chamber 18 or moisture cavity is defined by the interior of the sidewall 28 and the skin surrounding the user's eye 27 in sealed engagement with the first surface 35 of the body 20 of the mask 12 around the apertures 17 and in the area of the flange 13 which extends inward from the perimeter 33 edge of the body 20 of the mask 12. As noted the flange 13 portion has a width running a distance from the perimeter 33 to the base edge or circumference 26 of the sidewall 28 and for at least that width is preferably soft and flexible and at least slightly elastic to allow it to stretch and deform along the contours of the face of the user to achieve a good seal.

As shown in FIG. 1 the device 10 is formed to a mask 12 configuration, having a body 20 with a first extension 23 portion which extends toward and in front of the forehead of the user with the mask 12 in the as-used position. Also shown in FIG. 1, are optional moisture pads 30 which are specifically shaped to engage with the sidewall 28, within each chamber 18, out of the optic or straight-ahead view of the user to preserve unobstructed forward viewing through the transparent sidewall 28 during use.

For CPAP use, the first extension 23 may be employed in a sandwiched position between the CPAP device 21 components and the face and may be larger or smaller in size and area as required for such an engagement or for a fastener 17 engagement as noted above.

The pads 30, if employed, will supply a reservoir of moisture for hours to the chamber 18. Thermally reactive pads 30 may also be employed to provide warm moisture to comfort the user's eyes. Such thermal reactive pads 30 may have a chemically reactive center which is broken by bending the pad 30 by the user, and which generates heat or may also be configured for cooling.

Such pads could for instance employ pads with sodium acetate, glycerin, gel packs, cold water packs, etc. to provide cold, or heat, or moisture all depending on user need and whether the device is engaged in combination with a CPAP device or employed by users with other eye drying issues such as being adjacent moving air.

Shown in FIG. 2 is another mode of the device 10 which employs a face mask 12 having a body 20 formed of flexible elastic material such as a polymeric material or silicone, or other material which is pliable and soft so as to comfortably conform to contours of an engaged face and form seals of the flange 13 with the skin surrounding each eye. The chambers 18 or moisture cavities are also formed by a transparent sidewall 28 in the sealed engagement with the body 20 at the base edge or circumference 26 of the sidewall 28 with the eye-surrounding apertures 31 which are in registered positions to surround each eye. As indicated the sidewall 28 and body 20 and flange 13 may be formed of a unitary structure of the same material. Also, as noted it is preferred in all modes of the device 10 that the sidewall 28 be soft deformable material which will deform if placed between the user's face and bedding, but which will have sufficient memory shape from the curved formation or otherwise to return to the curved configuration projecting away from the second side surface 43 of the body 20 which is positioned opposite the first side surface 35 which contacts the face of a user.

As noted, while preferable transparent and optically correct to allow easy and unimpaired vision therethrough for users, especially when sleeping, the sidewall 28 may be tinted if the user is treating other issues concerning unclosed eyes during sleeping. Such as noted may be on airplanes in other venues where a tinted or opaque sidewall 28 will provide a benefit from surrounding light.

In cases where some moisture is required, but air passage is also desired, apertures 39 may be formed in the sidewall 28 to provide air passage to the chamber 18 however. The apertures 39 should be formed adjacent the body 20 of the mask 12 on a lower edge of the curved sidewall 28 opposite the side of the nose of the user so that the curve and projection of the sidewall 28 still blocks any airstreams emitted by the CPAP mask or a proximate fan or moving airstream, and from cold temperatures or air which is dry in nature.

The shielding eye mask 12 herein can be configured for operative engagement in combination with the CPAP mask, as noted using separable or inseparable fasteners 17 or combinations thereof. In that mode, the body 20 is configured to be placed in the as-worn position at the same time as the CPAP mask is placed properly on the face. Alternatively, the mask 12 can be engaged separately, or can be configured to be a unitary structure as part of a CPAP mask.

In one mode of the device 10 shown in FIG. 2, a second extension 15 from the flange 13 of the flexible body 20 of the mask 12, may be positioned to align with the bridge of the user's nose, with the mask in the as-worn position. This second extension 15 provides a pad interface between the contact of the CPAP mask with the nose which is a reported issue with many users, and makes the CPAP 21 mask more comfortable to wear. Further it provides, as noted, one means for removable engagement of the mask 12 with a CPAP 21 by forming a sandwiched engagement of a portion of the mask 12 between the face and CPAP 21 device. As noted FIG. 3 is a front perspective view of another mode of the mask 12 device 10 similar to that of FIGS. 1 and 2. In FIG. 3 is shown the second extension 15 having a larger width allowing a bending of the second extension 15 over a larger area of the nose in a curve similar to that shown in FIGS. 8-10. Also shown is the first extension 23 from the planar flange 13 extending in an opposite direction. Both the first and second extension are employable for the noted sandwiched engagement with the face and the CPAP 21 device. FIG. 4 is a front perspective view of another mode of the mask 12 of FIGS. 1 and 2 but solely having a wider first projecting portion for additional padding when used with a CPAP 21 device.

Shown in FIG. 5 is a user attempting to sleep with a conventional CPAP 21 device engaged in an as-used position on the face. By CPAP 21 used herein is meant the hose engaged component covering the mouth or nose or both of the user along with the mounting straps and harnesses employed therewith to position the CPAP 21 device in the as-used mounted position on the user. Any engagement by fasteners 17 thereto is meant by a permanent or separable fastener located on any component of the CPAP 21 in position to attach to any portion of the body 20 of the mask 12, or to become in a sandwiched engagement therewith, or combinations thereof.

In FIG. 6 is shown the user as in FIG. 5 having a CPAP 21 device engaged using the straps and harness conventionally employed to hold it in the as-used position. In this figure the device 10 herein is shown engaged in a combination with the CPAP 21 device by one or a combination of a strap 14 or permanent or separable fasteners 17 engaged between the mask 12 body 20 and any component of the CPAP 21 device since each such CPAP 21 has slightly differing configurations, straps and harnesses which may easily be adapted to hold the mask 12 to the user using fasteners 17 and/or projections to form a sandwiched engagement of portions extending from the body 20 of the mask 12 between the CPAP 21 device and face.

Figure 7:
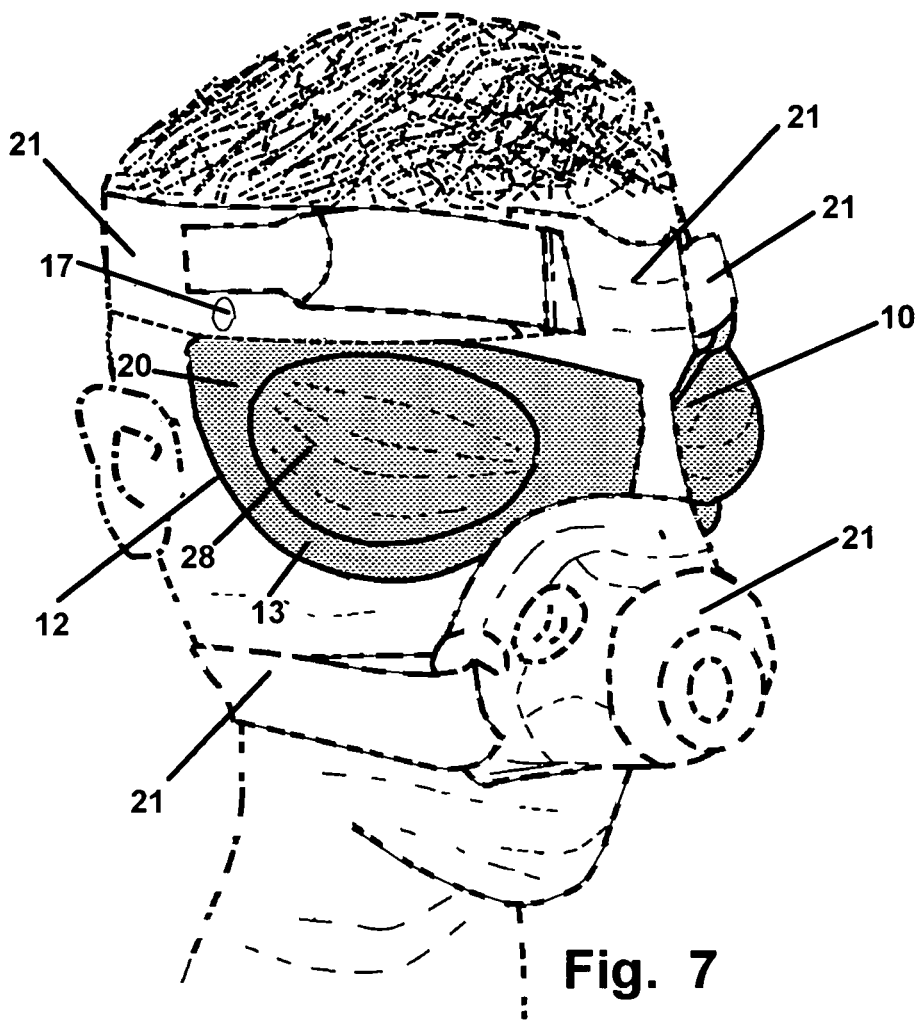
FIG. 7 depicts a user as in FIG. 6, and showing the device herein having the sealing flange and two chambers and being configured for an engagement to the as-used position in combination with a CPAP device.

FIG. 7 depicts a user as in FIG. 6, and showing the device 10 herein having the sealing flange 3 and two chambers 18 or moisture cavities in a user engagement in an as-used position in combination with a CPAP 21 device. The CPAP 21 device is shown engaged using the straps and harness conventionally employed to hold it in the as-used position. In FIG. 7, the device 10 herein is shown engaged in a combination with the CPAP 21 device by separable fasteners 17 engaged between the mask 12 and any component of the CPAP 21 device since each such CPAP 21 has slightly differing configurations, straps and harnesses which may easily be adapted to hold the mask 12 using fasteners 17. As shown so engaged, a respective one each of the curved sidewalls 28 is positioned in front of an eye of the user to thereby position a respective chamber or moisture cavity in sealed engagement with each eye.

Figure 8:
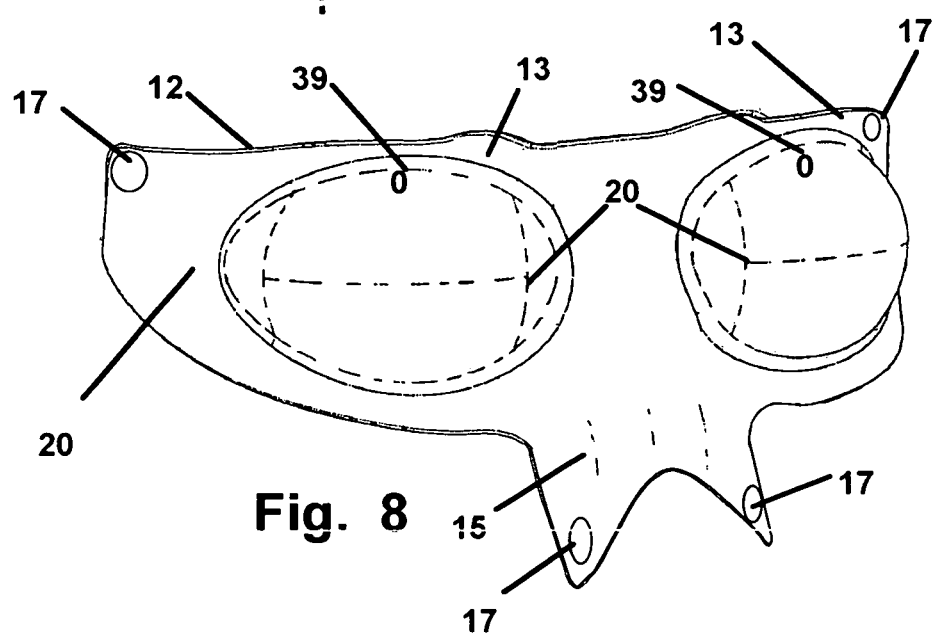
FIG. 8 shows a mode of the device having separable fastener halves with mater to complimentary fastener halves positioned on a CPAP device for use in combination therewith.

FIG. 8 depicts a user as in FIG. 6, having the device 10 herein having portions of the body 20 in an engagement with the CPAP 21 with a fastener 17 and also with a sandwiched engagement of upper and lower edge portions of the body 20 in-between the CPAP 21 components and the face of the user. This positions the apertures 39 formed through the body 20 to provide the sealed chamber in front of each eye concurrent with the engagement of the CPAP 21 to an as-used position on the face of the user.

In FIG. 8 is shown a mode of the device 10 having fasteners 17 where one half of separable fastener halves are positioned on the body 20 of the mask 12 in positions to register with and engage complimentary fastener 17 halves positioned on the components of the CPAP 21 device (FIG. 7) for use in combination therewith.

Figure 9:
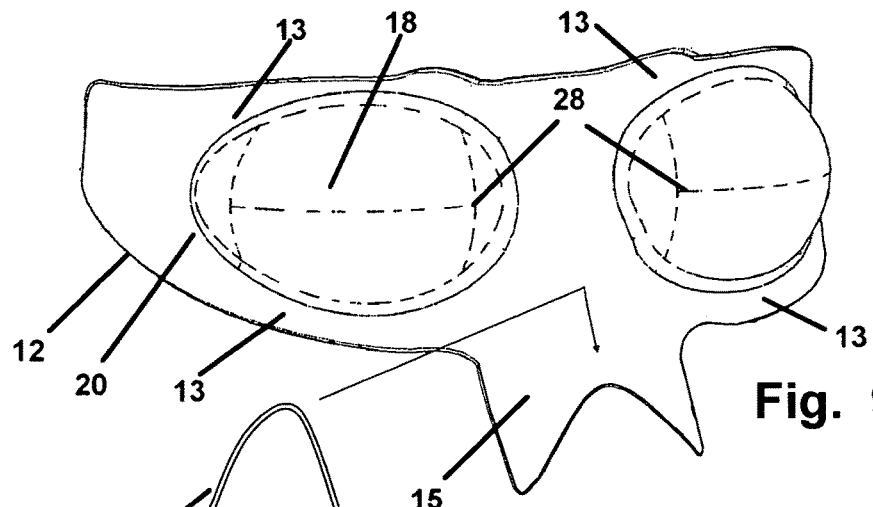
FIG. 9 shows the device configured to engage with a malleable or formable clip which engages over a projecting portion extending from the flange.
Figure 10:
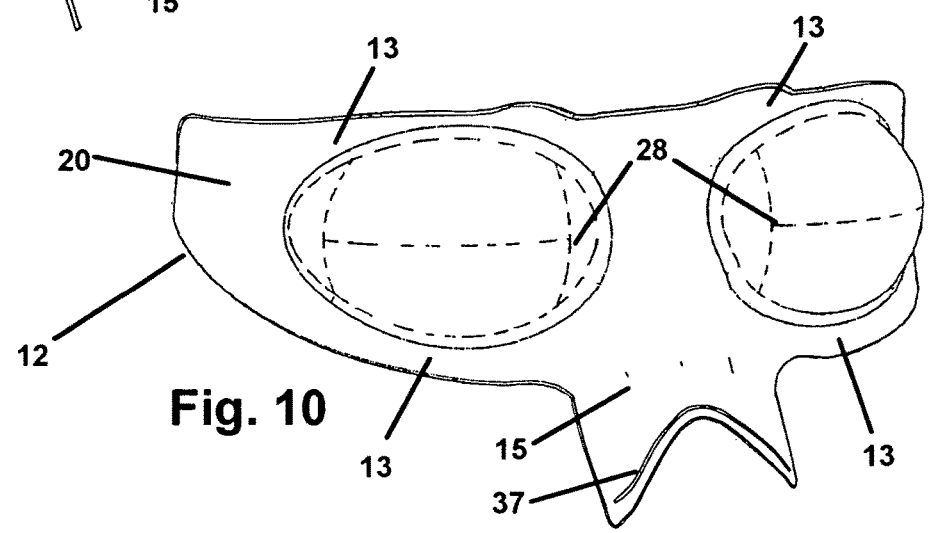
FIG. 10 depicts the device of FIG. 9, but with the user formable clip engaged within the projection portion.

FIG. 9 depicts the device 10 configured for use without the CPAP 21 device and having a malleable or formable clip 37 configured for the user to engage over a projecting second extension 15 extending from the body 20 of the mask 12. Once the projection second extension 15 is positioned above the bridge of the nose, the clip 37 may be engaged thereon to hold the second extension 15 sealed along the contours of the nose of the user. The clip 37 or clips 37 may be formed into the body 20 of the mask 12 as shown in FIG. 10.

Figure 11:
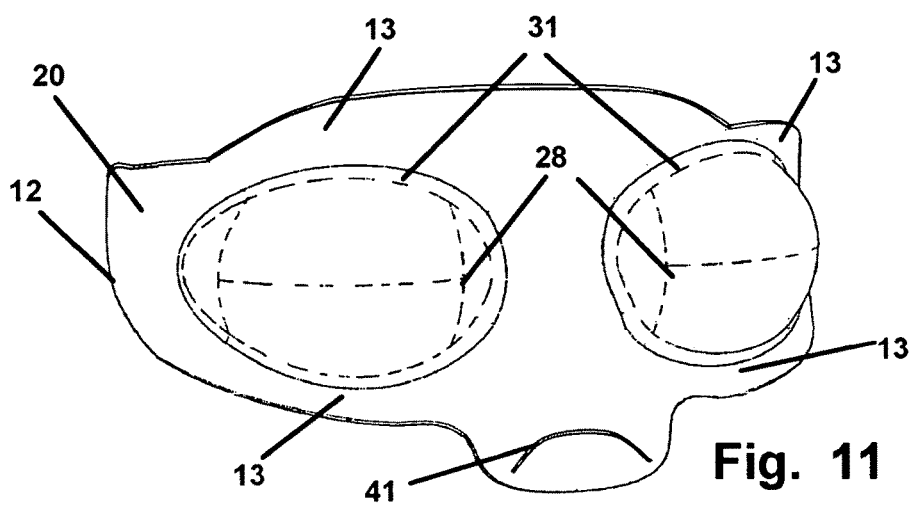
FIG. 11 shows a mode of the device having a first projecting portion to pad the nose of the user which includes a raised ridge configured to engage a recess in a CPAP mask and a secondary projection portion extending for engagement with the CPAP device above the eyes of the user.

In FIG. 11 is depicted a mode of the device 10 having a body 20 of the mask 12 with a raised ridge 41 extending from the second surface of the body 20 of the mask 12. This ridge 41 is dimensioned to engage a complimentary shaped recess (not shown) in a CPAP 21 device so as to maintain the sealed mask of the CPAP 21 device in a substantially fixed and registered positioning with the body of the mask 12 during use. Of course multiple ridges 41 might be employed in positions to register with multiple recesses and the positions of both the recesses and ridges 41 on the marks 12 and CPAP 21 could be reversed.

While all of the fundamental characteristics and features of the device 10 herein have been disclosed and described, with reference to particular embodiments thereof, a latitude of modification, various changes and substitutions are intended in the foregoing disclosure and it will be apparent that in some instance, some features of the facemask invention will be employed without a corresponding use of other features without departing from the scope of the invention as set forth. It should be understood that such substitutions, modifications, and variations may be made by those skilled in the art without departing from the spirit or scope of the invention. Consequently, all such modifications and variations are included within the scope of the invention as defined herein.

What is claimed is:

1. An apparatus for maintaining a moisture cavity adjacent each eye of a user, comprising:
  a mask, said mask having a flexible body having a first surface opposite a second surface both extending to a perimeter edge;
  a pair of apertures communicating through said body on opposite sides of a central portion of said body located therebetween;
  a pair of curved sidewalls, each in a sealed engagement at a circumferential base edge thereof to said body in respective aligned positions with one of each of said apertures;
  a first extension having a first end engaged with said body at said central portion thereof;
  said first extension projecting from said perimeter edge of said body to a distal end of said first extension;

said body positionable to an as-used position with said first surface in a contact against a face of a user and having one each of said pair of apertures aligned with a respective eye of said user;

said body in said as-used position positioning said first extension in an aligned position with a bridge of a nose of said user with a portion of said first extension extending along said nose in-between said bridge and a tip of said nose, with opposing sides of said extension in respective contacts with sides of said nose located in-between said bridge and said tip thereof;

said contact of said first surface against said face of said user said body forming a seal of said first surface of said flexible body against said face of said user which surrounds each of said apertures;

each said curved sidewall forming a moisture cavity; and wherein with said body positioned to said as-used position, each said moisture cavity maintains a moist interior air supply therein, and said first extension is is positioned for a removable engagement with a CPAP mask operatively positioned upon said user.

2. The apparatus for maintaining a moisture cavity adjacent each eye of a user of claim 1 wherein said removable engagement of said first extension with said CPAP mask is a sandwiched positioning of said first extension in-between said CPAP mask and said face of said user.

3. The apparatus for maintaining a moisture cavity adjacent each eye of a user of claim 1 wherein said removable engagement of said first extension with said CPAP mask comprises fasteners having separable fastener halves positioned on said first extension located in positions to register with and engage with complimentary fastener halves which are positioned on said CPAP mask.

4. The apparatus for maintaining a moisture cavity adjacent each eye of a user of claim 1 wherein each said sidewall is formed of pliable material which deforms from a curved shape during contact thereof with bedding supporting said face of said user, and which returns to said curved shape upon cessation of such contact.

5. The apparatus for maintaining a moisture cavity adjacent each eye of a user of claim 2 wherein each said sidewall is formed of pliable material which deforms from a curved shape during contact thereof with bedding supporting said face of said user, and which returns to said curved shape upon cessation of such contact.

6. The apparatus for maintaining a moisture cavity adjacent each eye of a user of claim 3 wherein each said sidewall is formed of pliable material which deforms from a curved shape during contact thereof with bedding supporting said face of said user, and which returns to said curved shape upon cessation of such contact.

7. The apparatus for maintaining a moisture cavity adjacent each eye of a user of claim 1 additionally comprising:

a secondary extension having a first end thereof engaged with said body at said central portion and projecting away from said perimeter of said body in an opposite direction to that of said first extension, to a distal end of said secondary extension; and said body in said as-used position positioning a portion of said secondary extension in-between said first end and a second end thereof, in contact with a forehead of said user.

8. The apparatus for maintaining a moisture cavity adjacent each eye of a user of claim 2 additionally comprising:

a secondary extension having a first end thereof engaged with said body at said central portion and projecting away from said perimeter of said body in an opposite direction to that of said first extension, to a distal end of said secondary extension; and said body in said as-used position positioning a portion of said secondary extension in-between said first end and a second end thereof, in contact with a forehead of said user.

9. The apparatus for maintaining a moisture cavity adjacent each eye of a user of claim 3 additionally comprising:

a secondary extension having a first end thereof engaged with said body at said central portion and projecting away from said perimeter of said body in an opposite direction to that of said first extension, to a distal end of said secondary extension; and said body in said as-used position positioning a portion of said secondary extension in-between said first end and a second end thereof, in contact with a forehead of said user.

10. The apparatus for maintaining a moisture cavity adjacent each eye of a user of claim 4 additionally comprising:

a secondary extension having a first end thereof engaged with said body at said central portion and projecting away from said perimeter of said body in an opposite direction to that of said first extension, to a distal end of said secondary extension; and said body in said as-used position positioning a portion of said secondary extension in-between said first end and a second end thereof, in contact with a forehead of said user.

11. The apparatus for maintaining a moisture cavity adjacent each eye of a user of claim 5 additionally comprising:

a secondary extension having a first end thereof engaged with said body at said central portion and projecting away from said perimeter of said body in an opposite direction to that of said first extension, to a distal end of said secondary extension; and said body in said as-used position positioning a portion of said secondary extension in-between said first end and a second end thereof, in contact with a forehead of said user.

12. The apparatus for maintaining a moisture cavity adjacent each eye of a user of claim 6 additionally comprising:

a secondary extension having a first end thereof engaged with said body at said central portion and projecting away from said perimeter of said body in an opposite direction to that of said first extension, to a distal end of said secondary extension; and said body in said as-used position positioning a portion of said secondary extension in-between said first end and a second end thereof, in contact with a forehead of said user.

13. The apparatus for maintaining a moisture cavity adjacent each eye of a user of claim 4 additionally comprising:

said pliable material forming sidewall is transparent and optically correct thereby forming a pliable lens providing unimpaired vision therethrough for said user.

14. The apparatus for maintaining a moisture cavity adjacent each eye of a user of claim 5 additionally comprising:

said pliable material forming sidewall is transparent and optically correct thereby forming a pliable lens providing unimpaired vision therethrough for said user.

15. The apparatus for maintaining a moisture cavity adjacent each eye of a user of claim 6 additionally comprising:
   said pliable material forming sidewall is transparent and optically correct thereby forming a pliable lens providing unimpaired vision therethrough for said user.

16. The apparatus for maintaining a moisture cavity adjacent each eye of a user of claim 1 wherein both of said curved sidewalls and said body are formed in a unitary structure from a thermoplastic elastomer, said unitary structure having a thickness between 0.050 inches to 0.080 inches.

17. The apparatus for maintaining a moisture cavity adjacent each eye of a user of claim 4 wherein each said sidewall is formed of opaque material forming a shield preventing light transmission therethrough.

18. The apparatus for maintaining a moisture cavity adjacent each eye of a user of claim 5 wherein each said sidewall is formed of opaque material forming a shield preventing light transmission therethrough.

19. The apparatus for maintaining a moisture cavity adjacent each eye of a user of claim 6 wherein each said sidewall is formed of opaque material forming a shield preventing light transmission therethrough.

20. The apparatus for maintaining a moisture cavity adjacent each eye of a user of claim 1 wherein said pair of curved sidewalls include apertures opposite said first extension.

\* \* \* \* \*